United States Patent
Jiang (10) Patent No.: US 10,724,939 B2
(45) Date of Patent: Jul. 28, 2020

(54) RAPID SINGLE CELL BASED BIOLOGICAL CELL SORTER

(71) Applicant: Wenbin Jiang, San Ramon, CA (US)

(72) Inventor: Wenbin Jiang, San Ramon, CA (US)

(73) Assignee: Cytek Biosciences, Inc., Fremont, CA (US)

(*) Notice: Subject to any disclaimer, the term of this patent is extended or adjusted under 35 U.S.C. 154(b) by 504 days.

(21) Appl. No.: 15/187,660

(22) Filed: Jun. 20, 2016

(65) Prior Publication Data

US 2016/0299053 A1    Oct. 13, 2016

Related U.S. Application Data

(62) Division of application No. 13/308,751, filed on Dec. 1, 2011, now Pat. No. 9,394,511.

(60) Provisional application No. 61/419,873, filed on Dec. 5, 2010.

(51) Int. Cl.
| | | |
|---|---|---|
| *G01N 15/14* | (2006.01) | |
| *C12M 1/00* | (2006.01) | |
| *B01L 3/00* | (2006.01) | |
| *G01N 15/00* | (2006.01) | |
| *G01N 15/10* | (2006.01) | |

(52) U.S. Cl.
CPC .... *G01N 15/1484* (2013.01); *B01L 3/502715* (2013.01); *B01L 3/502761* (2013.01); *C12M 47/04* (2013.01); *G01N 15/1434* (2013.01); *B01L 2200/0652* (2013.01); *B01L 2300/0654* (2013.01); *B01L 2300/0816* (2013.01); *B01L 2300/12* (2013.01); *G01N 2015/0065* (2013.01); *G01N 2015/1006* (2013.01); *G01N 2015/144* (2013.01); *G01N 2015/149* (2013.01)

(58) Field of Classification Search
CPC ......... G01N 15/1484; G01N 15/1434; G01N 2015/0065; G01N 2015/1006; G01N 2015/144; G01N 2015/149; B01L 3/502715; B01L 3/502761; B01L 2200/0652; B01L 2300/0654; B01L 2300/0816; B01L 2300/12; C12M 47/04

See application file for complete search history.

(56) References Cited

U.S. PATENT DOCUMENTS

| | | | |
|---|---|---|---|
| 2008/0160622 A1* | 7/2008 | Su ................ | G01N 1/4044 436/86 |
| 2008/0187472 A1* | 8/2008 | Ahn ............... | B01F 5/0403 422/255 |
| 2008/0213821 A1* | 9/2008 | Liu ................ | B01L 3/502761 435/39 |

* cited by examiner

*Primary Examiner* — Gailene Gabel
(74) *Attorney, Agent, or Firm* — Alford Law Group, Inc.; Vy H. Vu (57) ABSTRACT

A disposable rapid cell sorter comprises a microfluidic chip with electrodes and sorts biological cells of interest though a magnetic field and an electric field based on biological cell functional antibody bonded magnetic beads and luminescent labeling.

11 Claims, 6 Drawing Sheets

RAPID SINGLE CELL BASED BIOLOGICAL CELL SORTER

CROSS REFERENCE TO RELATED APPLICATIONS

This U.S. patent application is a divisional and claims the benefit of U.S. patent application Ser. No. 13/308,751, entitled, RAPID SINGLE CELL BASED BIOLOGICAL CELL SORTER, filed on Dec. 1, 2011 by Wenbin Jiang, issued as U.S. Pat. No. 9,394,511 on Jul. 19, 2016. U.S. patent application Ser. No. 13/308,751 claims the benefit of U.S. Provisional Patent Application No. 61/419,873 entitled RAPID SINGLE CELL BASED BIOLOGICAL CELL SORTER, filed on Dec. 5, 2010 by Wenbin Jiang.

FIELD OF INVENTION

The present invention generally relates to cell sorters; and more particularly, cell sorters that can be used to sort cells of interest for bio-medical applications.

BACKGROUND

Embryonic stem cells possess the ability to remain undifferentiated and propagate indefinitely in culture while maintaining their normal karyotypes and pluripotency to differentiate into the derivatives of all three embryonic germ layers (i.e. endoderm, mesoderm and ectoderm), including such highly specialized cells as neurons, pancreatic and heart cells, etc. that do not normally regenerate in vivo. In vitro differentiation, which is required for therapeutic applications, remains a stochastic process that non-specifically generates all the three germ layers and their derivatives to varying degrees. It is therefore necessary to purify the cell lineage of interest for clinical use. Similarly, adult stem cells for therapeutic applications can be harvested from various tissues of the human body (e.g. bone marrow, adipose tissue, etc.), but the cells need to be isolated and purified for therapeutic applications. Although first used for hematopoietic reconstitution, stem cells are now central to major efforts in regenerative medicine across multiple organ systems, including but not limited to; vascular, myocardial and neuronal repair. Central to all therapeutic efforts that utilize pluripotential stem cells is the ability to rapidly identify and non-destructively isolate individual cells using a cost effective process.

Developing of a cell based screening assay often requires identification and isolation of particular cells from a mixture of various kinds of cells. Moreover, in order to obtain reproducible data on cells and their use in cell-based therapies, reliable and non-destructive purification of cells is essential. Multiple cell isolation and purification techniques are being used in stem cell arena. Currently, magnetic-activated cell separation (MACS) provides a parallel rapid method for cell purification. However, due to the limited specificity of single antibodies in this technique and the omni-present non-specific binding, the purity of cell purification is marginal. It is usually used as a pre-purification method. The cell by cell sorting method currently provides the highest purification rates because multiple signals can be used to increase specificity. Fluorescence activated cell sorters (FACS) using flow cytometry are widely used in research clinics for cell isolation and purification. In a typical flow cytometer(1,2), individual particles pass through an illumination zone, typically at a rate of some 10,000 cells per second, and appropriate detectors, gated electronically, measure the magnitude of a pulse representing the extent of light scattering or fluorescence from labeled antibodies. The FACS instrument combines two basic functions: cell analysis and cell sorting. Fluorescence from labeled antibodies bound to cell surface markers is analyzed on a cell by cell basis in the analysis portion. The cell population of interest is then further sorted into a separate port and accumulated by electrically deflecting the flow stream. The essential character of the flow cytometric approach is strictly quantitative. The large number of available fluorescent antibody tags makes flow cytometry a unique tool for cell analysis and sorting.

Figure 1:
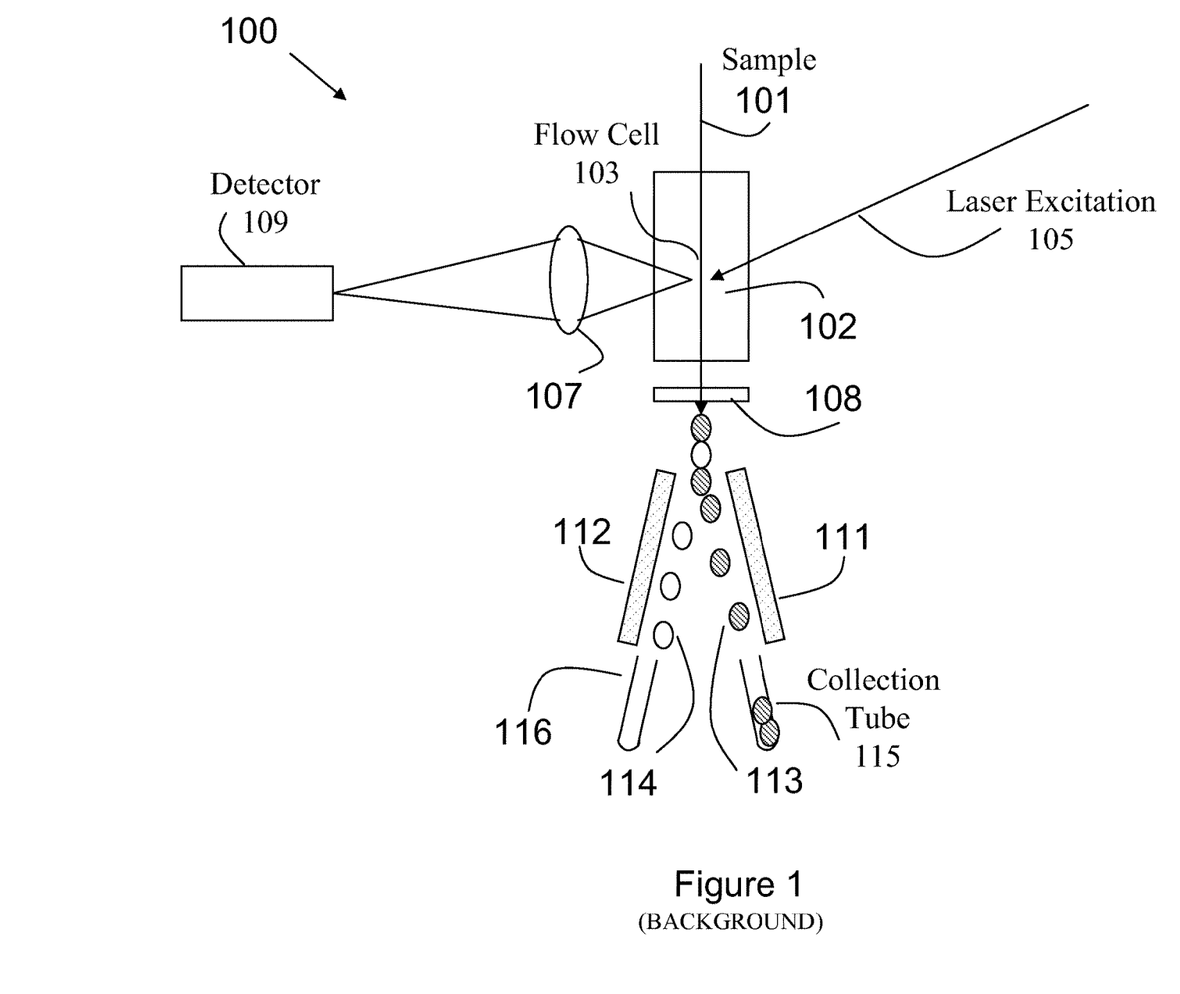
FIG. 1 is the configuration of a conventional cytometry for cell sorting.

FIG. 1 shows the schematic diagram of a conventional flow cytometric cell sorting system 100. A cell 103 passes the interrogation zone 102, where it is excited by laser beam 105 and its light scattering and fluorescence is collected by lens 107 and received by detection system 109. Typically, the flow cell 103 is vibrated at some 10 s of kHz to ensure that a uniform stream of droplets emerges from the end of the flow cell. The cell concentration is dilute enough so that the majority of droplets contain either zero or one cell. If a cell or droplet has been identified to be of interest, it is electrostatically charged by 108, causing the droplet to be deflected while passing a system of electrodes 111 and 112. The sorted cells 113 and 114 are collected by the collection tubes 115 and 116, respectively. Since the fluid with cells 103 is moving at a rate of 1 to 10 ms/droplet and the distance from the flow cell interrogation zone 102 to the deflector formed by the electrodes 111 and 112 is about 5 mm, the sorting decision needs to be made in less than 0.5 to 5 ms, allowing the sorting of some thousands of cells per second.

However, the rather bulky and complicated nature of the instrumentation as shown in FIG. 1 leads to fairly low adaptation rates in clinical labs. It is very difficult for a clinical lab to obtain appropriate approvals necessary to certify the cleanliness due to patient sample contamination in flow system for therapeutic applications. Current cytometer require careful and extensive cleaning procedures or exchanging of their sample handling components for this application, which requires a highly trained technician and can take many hours between running samples.

SUMMARY OF THE INVENTION

It is accordingly an object of the present invention to provide a cell sorting system which can solve the above problems in the prior art and can be made compact in size, high in the design flexibility, low in cost and high in reliability. It is also an object of the present invention to provide a cell sorting system to analyze cell function at individual cell basis and to sort cells in parallel based on cell functionality obtained individually.

In accordance with an aspect of the present invention, the above object is attained by providing a state-of-the-art disposable microfluidics-based cell sorting chip that eliminates the source contamination, which is critical for the required purity in stem cell research. Our design overcomes the speed issue due to cell by cell analyzing in microfluidic system. Instead of cell by cell serial analyzing and sorting, we invented a parallel single cell analyzing and sorting system for the needs of rapid cell analysis and sorting. The cell allows rapid parallel sorting relying upon CCD imaging, electric force capture and magnetic field release technologies. The iterative cost of this technology would be less than one tenth the cost of MACS technology, less than one tenth the iterative time of FACS technology and have increased mission/patient flexibility via both variable chip design parameters and secondary spectroscopic information available from the exciting laser.

BRIEF DESCRIPTION OF THE DRAWINGS

Representative elements, operational features, applications and/or advantages of the present invention reside inter alia in the details of construction and operation as more fully hereafter depicted, described and claimed—reference being made to the accompanying drawings forming a part hereof, wherein like numerals refer to like parts throughout. Other elements, operational features, applications and/or advantages will become apparent to skilled artisans in light of certain exemplary embodiments recited in the Detailed Description, wherein:

FIG. 3 (a) shows the concept of a cell sorting process based on a the present invention;

FIG. 3 (b) shows a side view of a cell sorting process based on the present invention;

Those skilled in the art will appreciate that elements in the Figures are illustrated for simplicity and clarity and have not necessarily been drawn to scale. For example, the dimensions of some of the elements in the Figures may be exaggerated relative to other elements to help improve understanding of various embodiments of the present invention.

Furthermore, the terms 'first', 'second', and the like herein, if any, are used inter alia for distinguishing between similar elements and not necessarily for describing a sequential or chronological order. Moreover, the terms front, back, top, bottom, over, under, and the like in the Description and/or in the claims, if any, are generally employed for descriptive purposes and not necessarily for comprehensively describing exclusive relative position. Skilled artisans will therefore understand that any of the preceding terms so used may be interchanged under appropriate circumstances such that various embodiments of the invention described herein, for example, are capable of operation in other orientations than those explicitly illustrated or otherwise described.

DETAILED DESCRIPTION OF THE DRAWINGS

The present invention will be explained with reference to the accompanying drawings, in which parts having the same reference numbers represent identical parts.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present invention, in addition to those not specifically recited, may be varied or otherwise particularly adapted by those skilled in the art to specific environments, manufacturing specifications, design parameters or other operating requirements without departing from the general principles of the same.

Further, unless expressly stated to the contrary, "or" refers to an inclusive or and not to an exclusive or. For example, a condition A or B is satisfied by any one of the following: A is true (or present) and B is false (or not present), A is false (or not present and B is true (or present, and both A and B are true (or present) Also, use of the "a" or "an" are employed to describe elements and components of the invention. This is done merely for convenience and to give a general sense of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the biological, chemical, and physical arts.

To the extent not described herein, many details regarding specific materials, processing acts, and circuits are conventional and may be found in textbooks and other sources within the fuel cell and chemical arts.

Figure 2:
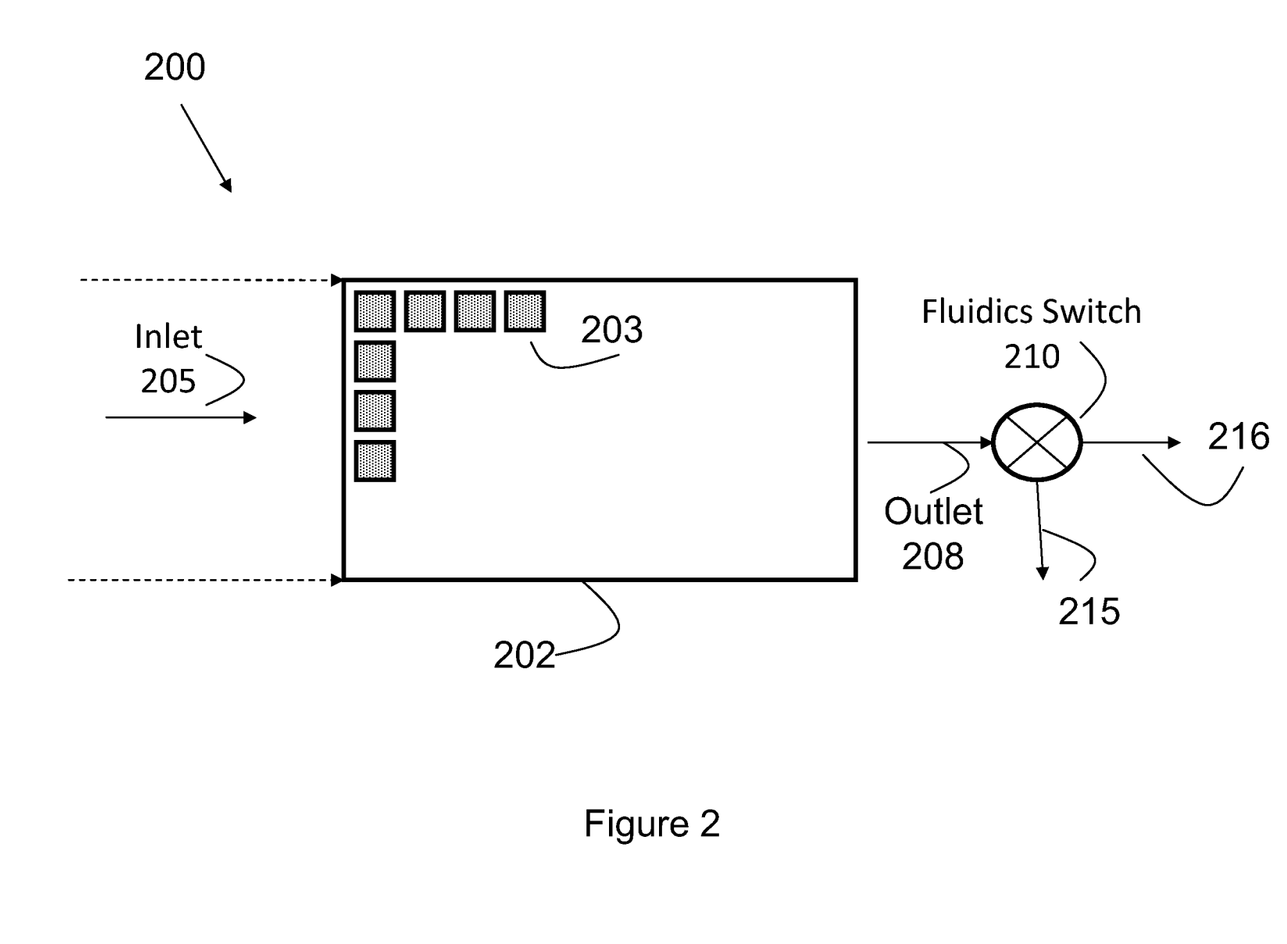
FIG. 2 is the schematic of a microfluidic cell sorter based on the present invention.

Turning now to FIG. 2, which is the schematic of a disposable parallel microfluidic cell sorter according to the current invention. The cell sorter 200 has a microfluidic chip 202 having a cavity, the cavity is transparent, flat, and hollow, which is made of glass, molded plastics, gel, ceramics, silicon, GaN, sapphire, or a combination of materials with at least one side of the wall transparent. In a preferred embodiment, microfluidic chip 202 is a glass chamber of 1 to 1000 µm high, 0.1 to 10 mm long and 0.01 to 10 mm wide. Preferably, it is 10 to 300 µm high, 1 to 3 mm long and 1 to 3 mm wide. On one of the microfluidic chip walls, preferably the bottom side, there deposits the metal electrode array 203. The metal can be transparent ITO film, Au, Al, Cu, or any other conductive materials that may adhere to the chip materials. The electrodes may be enclosed by polymers. Each cell of the metal array 203 has a dimension of 0.1 to 100 µm and preferably 10 to 50 µm on each side of the cell. The spacing between the electrodes is 0.1 µm to 100 µm, and preferably 5 µm to 20 µm. On the wall opposite to the one with the metal electrode array 203, there may deposit a blank transparent metal electrode, such as ITO, for generating electric field between the electrode array 203 and the transparent metal electrode inside the microfluidic chip 202. Chip 202 has a fluid inlet 205 and a fluid outlet 208. A fluidic switch 210 switches fluid flow between port 215 and port 216.

Figure 3A:
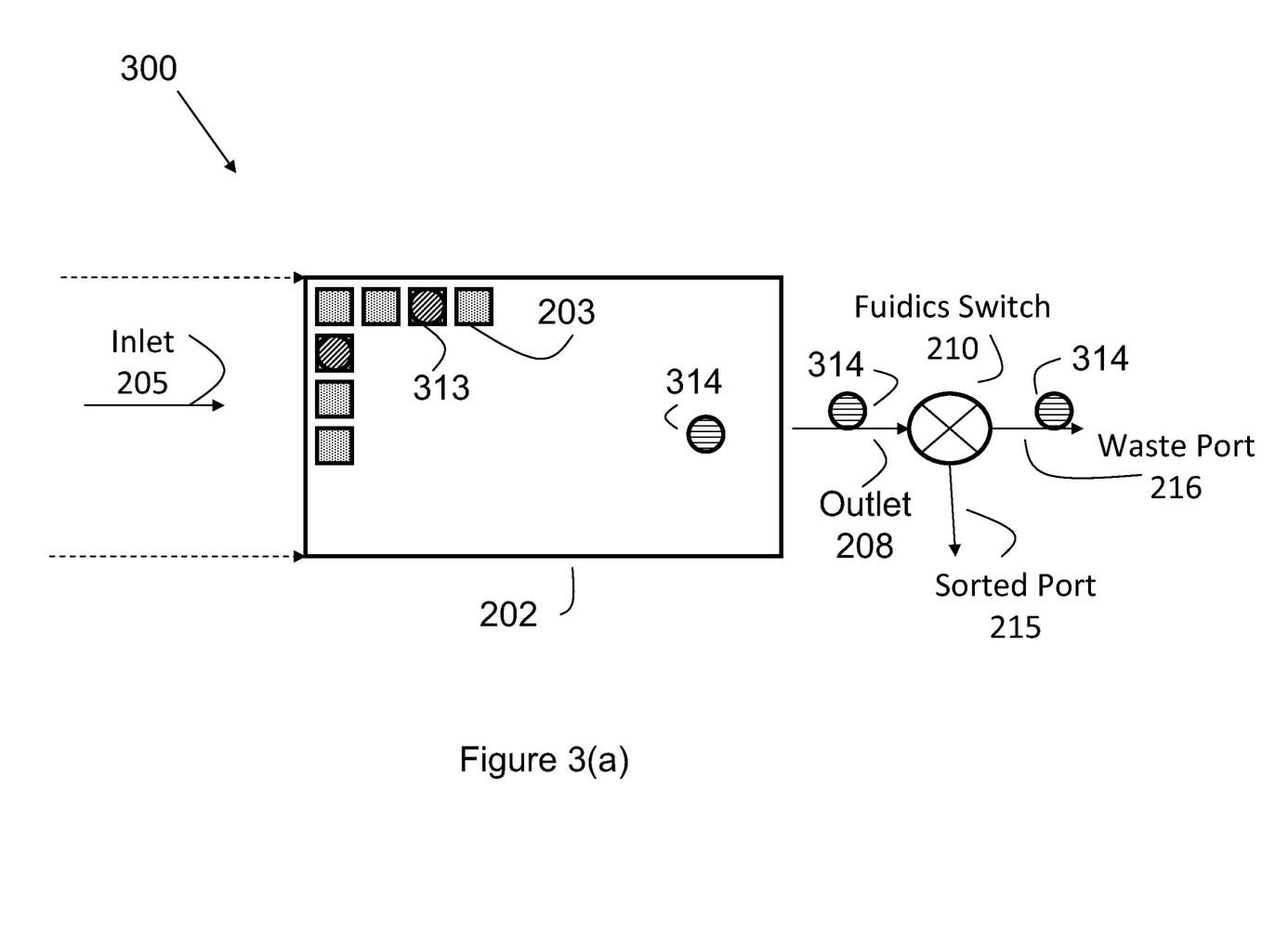
Figure 3B:
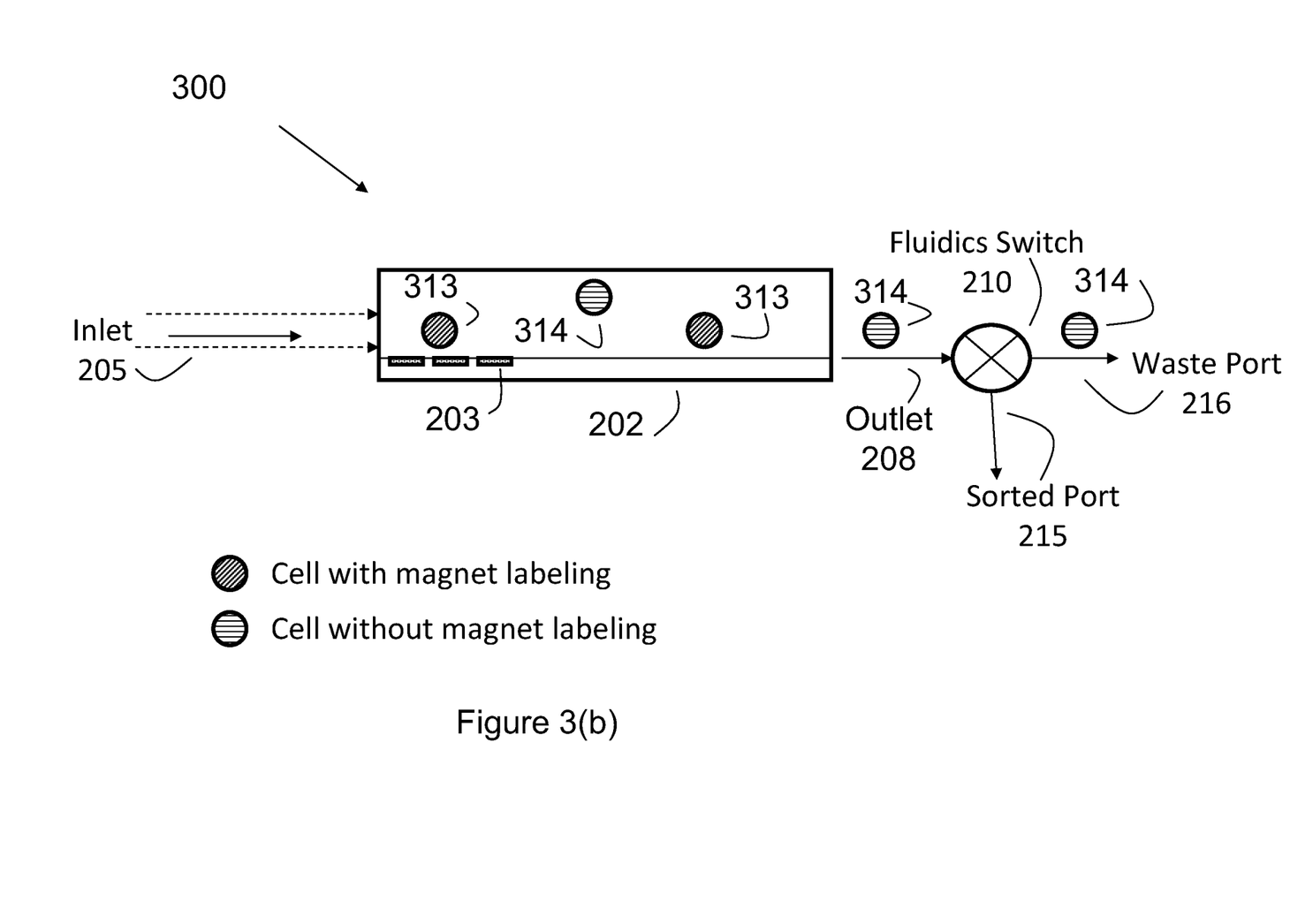
Figure 4:
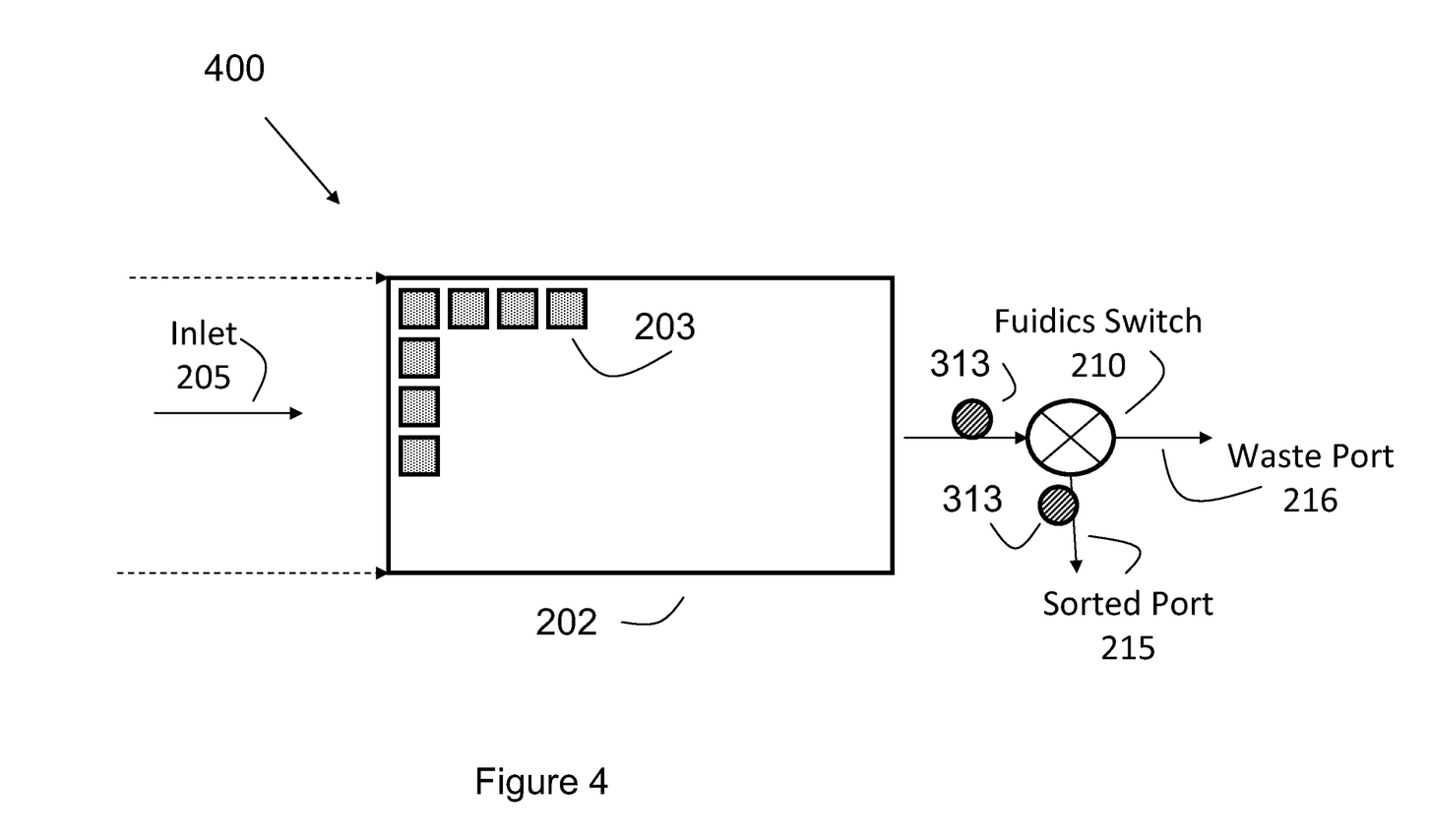
FIG. 4 shows the process of sorted cell collection based on the present invention.

FIG. 3(a) illustrates an operation principle of a disposable parallel cell sorter according to the present invention. A disposable parallel cell sorter 300 has a disposable microfluidic chip 202 having a cavity, the cavity is transparent, flat, and hollow with fluid inlet 205 and fluid outlet 208. Biological cells of interest 313, such as CD45, CD4, CD8, etc., and irrelevant cells 314 are carried by fluid and enter the chip 202 through inlet 205. Cells 313 are normally pre-bonded to magnetized beads through antibody on the beads. The magnetized beads are naturally charged. The magnetized beads are normally less than 1 μm and preferably less than 0.1 μm in diameter. Cells 314 are not bonded to any magnetized beads. When cells 313 and 314 enter the microfluidic chip 202, magnetic field applied to the chip 202 pulls cells 313 toward electrodes 203, as shown by the side view in FIG. 3(b). Cells 314 flow through outlet 208 and are collected by waste port 216 through fluid switch 210. Afterwards, cells of interest 313 are collected by sorted port 215 through fluid switch 210, as shown by system 400 in FIG. 4.

Figure 5:
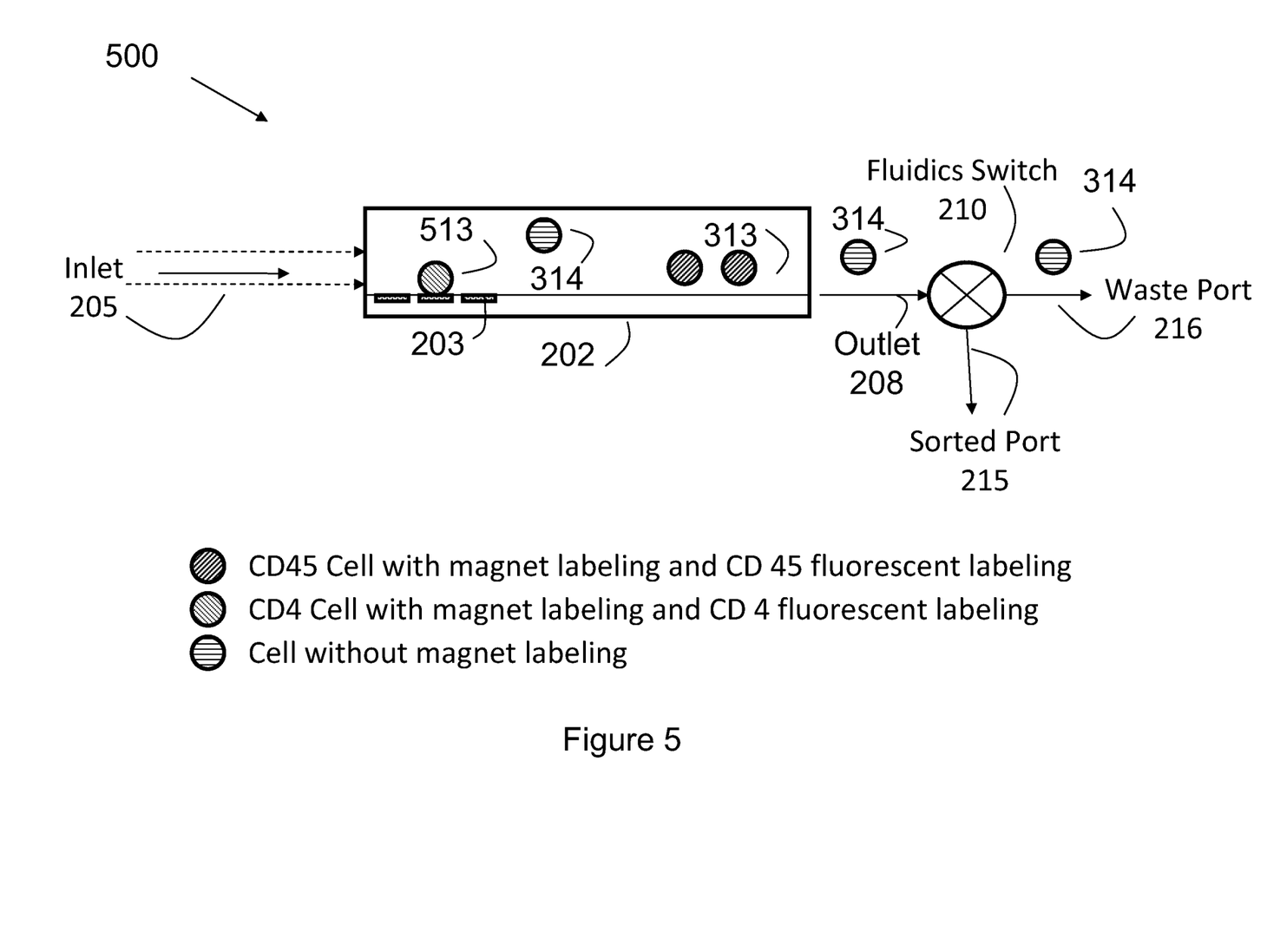
FIG. 5 shows the schematics of a cell sorter to sort cells using both a magnetic field and an electric field based on the present invention.

When a subcategory of cells 313, such as CD4 or CD8 among CD45, designated as cells 513 in FIG. 5, must be sorted, Antibodies of the cells are pre-labeled with specific luminescence signature and attached to the cells of interest. When the cells to be sorted, including 313, 513 and 314 are loaded into the microfluidic chip 202, magnetic field is applied to the chip 202 to pull cells 313 and 513 toward array electrodes 203, which is also an optical imaging plane of a detection system comprises of a lens or lenses and a detector or detector array, such as a CCD camera, PIN photodiode, APD, or PMT, which are not shown in the figure. Cells 313 and 513 lean against electrodes 202 randomly. An optical excitation system, such as a laser, is used to scan across the electrodes 202 to excite the luminescence of the cells. Cells 513 will generate specific luminescence and be detected. An electric field will be applied to the most adjacent cell of the electrode 202. As the magnetized beads of the cells are naturally charged, the electric field will force cells 513 to stay with electrode 203. This force is stronger than the magnetic force generated by the magnetic field, which pulls both cells 313 and 513 toward the optical imaging plane along the electrode 203. While a laser or LEDs can be used to excite the fluorescent antibody across the chip 202 electrodes 203, a spatially broadened laser beam can be used to excite all the cells within chip 202 simultaneously to increase the sorting rate. A two-dimensional detection system, such as a CCD camera, should be pre-calibrated to correlate the detection cells with the electrode cells 203, thus to synchronize the application of electric field on the cells that luminate.

When all the cells are characterized in chip 202, magnetic field is removed or flipped to allow cells 313 and 314 to exit outlet 208 and be collected into waste port 216. Sorted cells 513 remain staying with electrode 203 by the applied electric field.

Afterwards, there will be two paths to collect the sorted cells 513. The first approach is to turn off the electric field to allow cells 513 to exist outlet 208 and be collected into sorted port 215. The second approach is to keep cells 513 on the electrode 203 and new fluid is introduced into chip 202 to continue the sorting process. When electrode 203 is almost filled with sorted cells 513, chip 202 is taken off from the sorter as a sample for further characterization. Multiple photoluminescence labels can be applied to the correspondent antibodies to allow the sorting of multiple cells of interest in parallel using the same method described. The detection system should therefore be wavelength sensitive. A CCD camera with color filter is one example of a detection system that can be used to identify the wavelength of the luminescence. A memory map corresponding to the 2-D configuration of electrode 203 of the microfluidic chip is normally used to record the sorted cell position on chip 202 corresponding to the luminescence wavelength. There are multiple sorted cell collection ports connected to fluidic switch 210. When releasing sorted cells to the correspondent sorted cell collection port through fluidic switch 210, the 2-D electric field is withdrawn according to the memory map contents, thus, multiple biological cells can be sorted in parallel through multiple photoluminescence labeling.

To enhance the sorting efficiency and accuracy, magnetic field for sorting magnetically labeled cells can be generated by an array of micro-magnets, which can be controlled individually, thus increasing the cell sorting granularity. Also, photosensitive molecule or polymer may be introduced into the microfluidic chip to pre-attach to one of the wall of the chip. When a cell of interest is detected, a light can be used to bond the cell to the chip wall through the photosensitive molecule or polymer, thus adding one more dimension to the cell sorting process for parallel cell sorting with multi-signatures based on single cell detection. The same optical method can be used to debond the optically bonded cells for sending the sorted cells to the correspondent sorted port through fluidic switch.

When each metal electrode cell dimension is kept at 20 μm×20 μm, and chip dimension is at 3 mm×3 mm, the total number of cells that can be sorted per microfluidic chip is 22,500. Assuming the fluid dwelling time inside chip 202 is 1 second, the sorting rate of this cell sorter will be 22,500/sec. This cell sorting can be performed after pre-enrichment of cells by magnetic beads. Therefore, the effective cell sorting rate can exceed 1 million cells per second with the combination of pre-enrichment of cell of interests. This is equivalent to the current state of art cell sorting cytometry. Thus, the present invention has high practical effects. It function equally well for either positive or negative selection, providing yet another layer of mission/patient flexibility. Localization of the selection activity within a low cost chip is a practical, economical single use product that will eliminate the possibility of cross-contamination between iterations. It will be further possible to recycle chip material to decrease iterative costs and minimize environmental impact. In summary, this invention herein represents a more flexible technology that dramatically reduces the iterative time and cost of cell selection over currently available methodologies. This constellation of attributes is highly desirable for both clinical and research applications that require cell identification, enumeration, isolation/selection, or a combination thereof. This assures its application to a broad population of patients, clinical scenarios and research initiatives within Medical Oncology, Stem Cell Biology and Regenerative Medicine.

In the foregoing specification, the invention has been described with reference to specific exemplary embodiments; however, it will be appreciated that various modifications and changes may be made without departing from the scope of the present invention as set forth in the claims below. The specification and figures are to be regarded in an illustrative manner, rather than a restrictive one and all such modifications are intended to be included within the scope of the present invention. Accordingly, the scope of the invention should be determined by the claims appended hereto and their legal equivalents rather than by merely the examples described above. For example, the steps recited in any method or process claims may be executed in any order and are not limited to the specific order presented in the claims. Additionally, the components and/or elements recited in any apparatus claims may be assembled or otherwise operationally configured in a variety of permutations to produce substantially the same result as the present invention and are accordingly not limited to the specific configuration recited in the claims.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components of any or all the claims.

The present invention has been described relative to an illustrative embodiment. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific feature of the invention described herein, and all statements of the scope of the invention which, as a matter of language, might be said to fall therebetween.

I claim:

1. A method for rapidly sorting biological cells comprising:
providing magnetically labeled biological cells of interest, wherein the biological cells of interest are bonded to a first set of antibodies coupled to magnetic micro-beads, wherein the first set of antibodies are specific to cell surface antigen present on the biological cells of interest;
labeling a subset of the magnetically labeled biological cells of interest with a second set of antibodies that are bonded to a photoluminescence label to form a photoluminescence labelled subset of the magnetically labelled biological cells of interest, wherein the second set of antibodies are specific to cell surface antigen present on the subset of the biological cells of interest;
receiving a fluid through an inlet of a microfluidic chip, the fluid containing biological cells not magnetically labelled, the magnetically labelled biological cells of interest, and the photoluminescence labelled subset of the magnetically labelled biological cells of interest, forming a biological cell mixture to be sorted;
holding the fluid for cell sorting in a transparent hollow cavity of the microfluidic chip;
turning-on a magnetic field to sort the magnetically labelled biological cells of interest in the microfluidic cavity by aligning the magnetically labeled biological cells of interest in the fluid against one of the flat surfaces of the microfluidic chip inside the cavity;
exciting the photoluminescence label from the photoluminescence labelled subset of the magnetically labelled biological cells of interest using a light source;
detecting the photoluminescence signal from the photoluminescence labelled biological subset of the magnetically labelled biological cells of interest using a luminescence detection system; and
in response to detecting the photoluminescence signal in the subset of the magnetically labelled biological cells of interest, turning-on a two-dimensional addressable electric field closest to the photoluminescence labelled subset of the magnetically labelled biological cells of interest detected by the luminescence detection system to catch the photoluminescence labelled subset of the magnetically labelled biological cells of interest through an electric force applied to the magnetic micro-beads.

2. The method for rapidly sorting biological cells as claimed in claim 1 further comprising:
releasing the fluid with the biological cells not magnetically labeled through an outlet of the said microfluidic chip; and
collecting the biological cells not magnetically labeled into a first cell collection port through a fluid switch.

3. The method for rapidly sorting biological cells as claimed in claim 2 further comprising:
turning-off the magnetic field and releasing sorted magnetically labeled biological cells not electrically caught onto the microfluidic chip surface through the outlet and the fluid switch toward a second cell collection port.

4. The method for rapidly sorting biological cells as claimed in claim 3 further comprising:
turning-off the two-dimensional addressable electric field and releasing the sorted photoluminescence labelled subset of the magnetically labelled biological cells through the outlet and fluid switch toward a third collection port.

5. The method for rapidly sorting biological cells as claimed in claim 1 wherein,
the microfluidic chip is made of one of any of the following materials glass, plastics, gel, gallium-nitride (GaN), and/or sapphire having an array of conductive electrodes on one of the flat hollow cavity surfaces of the microfluidic chip for generating the two-dimensional addressable electric field extending into the microfluidic cavity according to an array electrode configuration.

6. The method for rapidly sorting biological cells as claimed in claim 1 wherein,
the biological cells of interest that are magnetically labeled are CD45 cells.

7. The method for rapidly sorting biological cells as claimed in claim 1 wherein,
the subset of biological cells that are both magnetically and photoluminescence labeled are CD4 and/or CD8 cells.

8. A method for rapidly sorting biological cells comprising:
receiving a fluid having a cell mixture, comprising magnetically labelled biological cells of interest to be sorted, through an inlet of a microfluidic chip;
holding the fluid for cell sorting in a transparent hollow cavity having at least a flat surface of the microfluidic chip;
immobilizing magnetically labelled biological cells of interest on the flat surface of the microfluidic chip inside the cavity using a first means of magnetic sorting, wherein the magnetically labelled biological cells of interest are bonded to a first set of antibodies specific to cell surface antigen present on the biological cells of interest and coupled to magnetic microbeads;
characterizing a subset of the immobilized magnetically labelled biological cells of interest using a luminescence detecting system in a second means of fluorescence sorting wherein the subset of magnetically labelled biological cells of interest are labeled with a second set of antibodies specific to cell surface antigen present on the subset of the biological cells of interest and coupled to a photoluminescence label; and
reinforcing the photoluminescence labeled subset of the immobilized magnetically labelled biological cells of interest by using the luminescence detecting system to activate a third means of electric field sorting according to characterization results produced by the second means.

9. The method for rapidly sorting biological cells of interest as claimed in claim 8 wherein the first means of magnetic sorting further comprises:

pre-labeling the biological cells of interest to be sorted with magnetic beads and immobilizing the magnetically labeled biological cells of interest using a magnetic field.

10. The method for rapidly sorting biological cells of interest as claimed in claim 8 wherein the second means further comprises:

pre-labeling the subset of the magnetically labelled biological cells of interest to be sorted with photoluminescence label;

exciting a specific photoluminescence from the photoluminescence labeled subset of magnetically labelled biological cells of interest using a light source across the immobilized magnetically labelled biological cells; and detecting a photoluminescence signal from the photoluminescence labeled subset of magnetically labelled biological cells of interest with a luminescence detection system.

11. The method for rapidly sorting biological cells of interest as claimed in claim 8 wherein the third means further comprises:

applying two-dimensional micro-electrodes to the flat surface of the microfluidic chip for the generation of an electric field penetrating into the microfluidic chip;

in response to detecting a photoluminescence signal using the second means of fluorescence sorting, turning-on the electric field to apply an electric force to reinforce the immobilization of the photoluminescence labeled subset of magnetically labelled biological cells of interest, characterized by the second means, at the location of the electrode according to the said characterization results.

* * * * *